United States Patent [19]

Takayama

[11] Patent Number: 4,499,895

[45] Date of Patent: Feb. 19, 1985

[54] ENDOSCOPE SYSTEM WITH AN ELECTRIC BENDING MECHANISM

[75] Inventor: Syuichi Takayama, Tokyo, Japan

[73] Assignee: Olympus Optical Co., Ltd., Tokyo, Japan

[21] Appl. No.: 434,233

[22] Filed: Oct. 14, 1982

[30] Foreign Application Priority Data

| Oct. 15, 1981 | [JP] | Japan | 56-164678 |
| Oct. 20, 1981 | [JP] | Japan | 56-167594 |
| Nov. 2, 1981 | [JP] | Japan | 56-176236 |

[51] Int. Cl.³ .............................................. A61B 1/06
[52] U.S. Cl. ........................................ 128/6; 318/305
[58] Field of Search ........................................ 128/4–8; 318/293, 305, 490; 74/425.5, 426, 473 P

[56] References Cited

U.S. PATENT DOCUMENTS

| 1,121,786 | 12/1914 | Barnum | 318/305 |
| 3,641,410 | 2/1972 | Vogelsberg | 318/305 |

FOREIGN PATENT DOCUMENTS

| 2504663 | 10/1977 | Fed. Rep. of Germany | 128/4 |
| 2713749 | 10/1977 | Fed. Rep. of Germany | 128/4 |
| 50-25083 | 3/1975 | Japan |  |
| 53345790 | 4/1976 | Japan |  |
| 1442487 | 7/1976 | United Kingdom | 318/305 |

Primary Examiner—Edward M. Coven
Assistant Examiner—Max E. Hindenburg

[57] ABSTRACT

An endoscope apparatus is disclosed which includes an insertion section inserted into a coeliac cavity of a human body and freely bendable therein, a motor housed in an operating section of an endoscope, a bending mechanism for bending a flexible tube of the insertion section on the basis of a torque of the motor, and a bending operating lever made of resilient material manually operated by an operator. When the operator operates the lever and deflects the lever, a piezoelectric rubber serving as wire distortion gauge attached to the lever is compressed or tensioned to change its resistance. At this time, the motor rotates to turn the drum, so that the flexible tube is bent through angulation wires. When the deflection of the lever mounted to the rotating drum disappears, the resistance change of the gauge is zero. Responsive to no change of the resistance, the motor stops its rotation. Consequently, the bending operation of the flexible tube rapidly stops.

11 Claims, 18 Drawing Figures

ENDOSCOPE SYSTEM WITH AN ELECTRIC BENDING MECHANISM

BACKGROUND OF THE INVENTION

The present invention relates to an endoscope system, and more particularly, to an endoscope system with an electric bending mechanism for electrically bending an insertion section.

In use, an insertion section of an endoscope is inserted into a coelom of a living body (such as a patient) and is bent in such a way as an operator (such as a doctor) desires for diagnosis. In recent years, there has been proposed an endoscope system with a motor-driven bending mechanism for electrically bending an insertion section including a flexible tube by means of a motor, for improving a bending operation of the insertion section of an endoscope.

In a practical use of the endoscope, which is designed for specific mechanical purposes, the insertion section of the endoscope is directly inserted into a coeliac cavity of a living body, such as the stomach, intestines and the like. In bending the insertion section of the endoscope in the coeliac cavity, great care must be taken so as not to impair the coelom. To this end, a subtle and precise control of the motor drive strictly according to the wishes of the operator is required for the bending operation of the endoscope insertion section. Further required is to accurately know an actual direction and an actual amount of the bending of the insertion section inserted and now present in the coelom. Otherwise, the distal end of the insertion section is excessively and uncontrollably bent to possible impair or, more adversely, break the inner wall of the coelom.

So far as we know, there have been no endoscope systems with a motor-driven bending mechanism which satisfactorily meet the technical requirements mentioned above. For example, an endoscope system disclosed in Japanese Utility Model Unexamined Publication No. 53-45790 is comprised of a motor, a manually operating member for controlling the drive of the motor, and a mechanical displacing member provided close to the operating member and mechanically displacing according to a bending angle of the insertion section of the endoscope. In order to know an actual amount of the bending of the insertion section in the coelom, an operator must contact the displaced member by hand. The prior endoscope mechanism employs a mechanical means for detecting the actual bending angle of the insertion section. Because of the nature of the mechanical means, it is very difficult to reliably and accurately control the bending operation of the insertion section in quick response to the operator's wishes. The mechanical means employed in the prior endoscope system needs a number of mechanical parts and a complex assembly of these parts. This results in a complicated structure of the endoscope system. It is therefore very difficult to obtain satisfactory reliability in the bending control of the insertion section of such an endoscope apparatus.

SUMMARY OF THE INVENTION

Accordingly, an object of the present invention is to provide an endoscope apparatus with a motor-driven bending mechanism which may reliably and accurately control the bending operation of its insertion section in quick response to the directions of an operator, thus ensuring the safety of the living body into which it is inserted.

In an endoscope apparatus in accordance with the present invention, an insertion section and an endoscope body frame are mechanically coupled to each other. The insertion section is properly bendable in a coeliac cavity of a living body such as a patient when the insertion section is inserted into the coeliac cavity. A motor device is provided or housed in the endoscope body frame to generate a rotating torque for bending the insertion section. A bending device which is provided in the body frame and the insertion section is connected to the motor device and the insertion section to bend the insertion section by the rotating torque transferred from the motor device. An operation lever member is provided in the endoscope body frame with a slight protrusion from the body frame so as to allow a manual operation thereof. The endoscope apparatus also comprises a control circuit which is electrically connected to the motor device. The control circuit allows power supply to the motor device in response to the operation by the lever member, and electrically recognizes the degree of the lever operation and the degree of bending of the insertion section to electrically detect a time point at which the increasing bending amount of the insertion section is equal to a given amount substantially corresponding to the level operation amount. Whereby, the power supply to the motor device is shut off to stop the bending operation of the insertion section of the endoscope apparatus.

BRIEF DESCRIPTION OF THE DRAWINGS

The present invention is best understood by reference to the accompanying drawings, in which.

DETAILED DESCRIPTION OF THE PREFERRED EMBODIMENT

Figure 1:
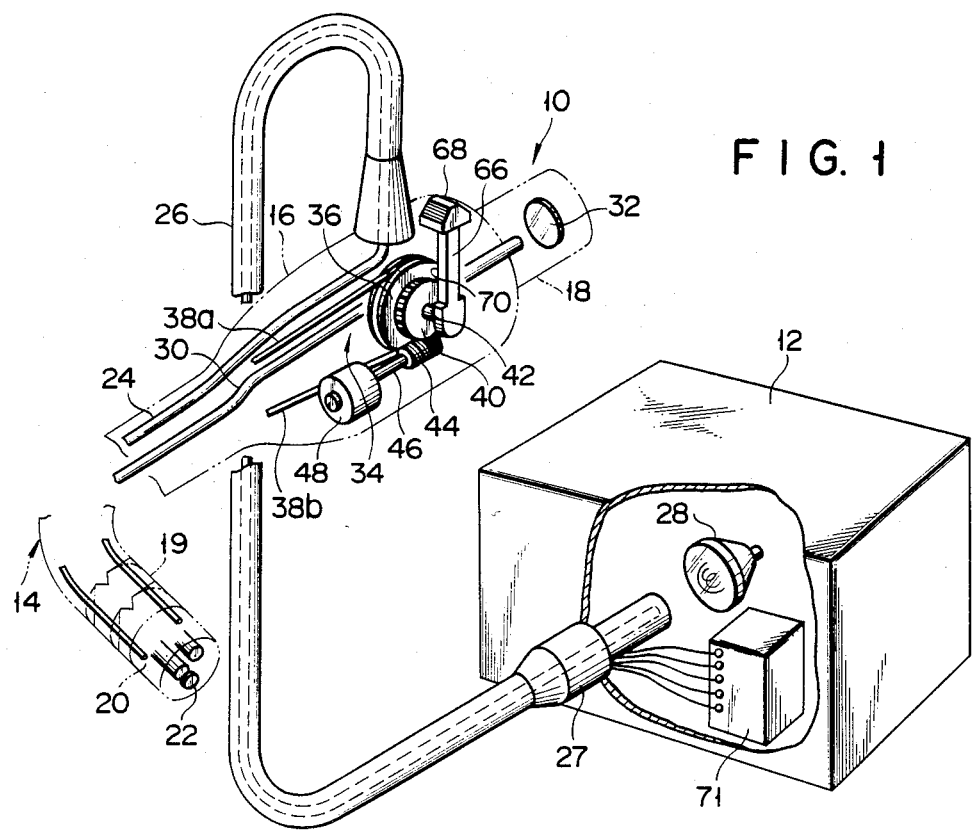
FIG. 1 is a perspective view of an overall endoscope system which is a first embodiment of the present invention.

Referring now to FIG. 1, an endoscope system includes an endoscope apparatus 10 and a light source apparatus 12. The endoscope system 10 is comprised of an insertion section 14 to be directly inserted into the coeliac cavity of a living body, a main body section or an operating section 16 mechanically coupled to the insertion section 14 and having a variety of switches (not shown), and an ocular section 18 mounted to the operating section 16. The insertion section 14 includes a flexible tube 19 bendable in a desired direction, and an end section 20 with a known structure mounted to the free end of the tube 19, which has a window (not shown) for allowing the passage of light rays and contains therein an objective lens 22. A light guide 24 using a bundle of optical fibers for transmitting light rays containing the data under observation is inserted into the insertion section 14 and the operating section 16, and extends at one end into the end section 20. In the end section 20, the one end of the light guide 24 is positioned close to the objective lens 22. The light guide 24 is further passed through a cord coupled with the operation section 16. This cord is known as a light guide cord or a universal cord by those skilled in the art. A connector 27 of the universal cord 26 is removably connected to the light source apparatus 12 in a known manner. The other end of the light guide 24 extending through the universal cord 26 is positioned facing a light source, or a lamp 28, in a light source apparatus 12 when the cord 26 is coupled with the light source apparatus 12 through the connector 27. Further, the positioning of the other end of the light guide 24 is made in such a way that it may effectively receive the light rays emitted from the lamp 28.

An image guide 30 for transmitting the reflected light from the inner surface of the coelom to which light rays are projected through the window of the end section 20 is formed of a bundle of optical fibers. The image guide 30 is passed through the insertion section 14 and the operation section 16 to extend into the ocular section 18. In the ocular section 18, the image guide 30 is positioned at one end close to an objective lens 32. Since the optical fibers forming the light guide 24 and the image guide 30 are made of flexible light transmission material, the optical fibers may properly bend with the bending of the flexible tube 19 in the insertion section 14.

The operating section 16 of the endoscope contains a mechanism for an operator such as a doctor to remotely control the bending of the flexible tube 19 for changing the direction of the end section 20 in the coeliac cavity, such as the stomach or intestines, for diagnosing, inspecting or treating the patient. The bending control mechanism 34 includes a continuous groove on the peripheral surface of the mechanism per se and a drum 36 freely rotatable in the forward or reverse direction. A wire 38 is wound around the groove of the drum 36. Wires (angulation wires) 38a and 38b are led through the operating section 16 and the insertion section 14, and the ends thereof are fixed to the end section 20. With rotation of the drum 36, the angulation wires 38a and 38b are pulled to bend the flexible tube 19 and to change the end section 20 in a desired direction.

A gear 40 is fixed to a shaft 42 of the drum 36. The gear 40 is in mesh with a worm gear 44 mounted to a rotating shaft 46 of the electric motor 48. Accordingly, the drum 36 rotates selectively forwardly or backwardly with the rotation of the motor 48. Thus, the flexible tube 19 may be bent in a desired direction by the combination of the gears 44 and 40, the drum 36 and the wire 38, which is driven by a rotating torque of the motor 48.

Figure 2:
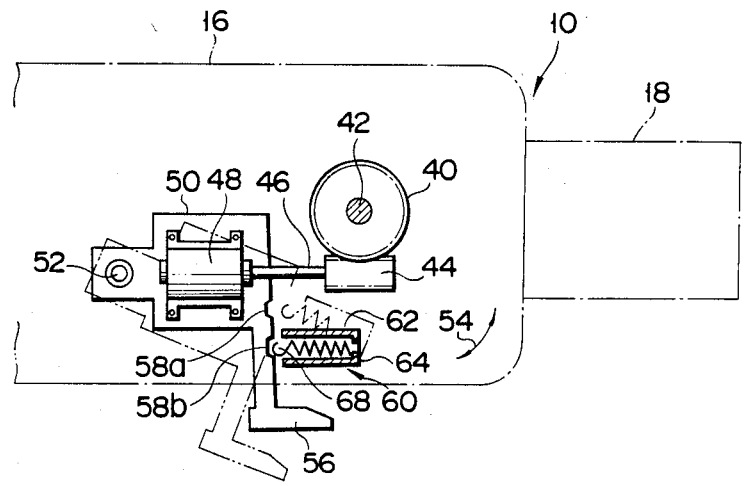
FIG. 2 illustrates a structure of the peripheral portion of a motor provided in the endoscope system of FIG. 1.

The peripheral portion of the motor 48 shown in FIG. 1 is illustrated in detail in FIG. 2. The motor 48 is fixed to a support plate 50 mounted rotatably in the direction 54 through a pin 52 at a given location in the operating section 16. An operation lever 56 partially projecting outside the operating section 16 is formed integral with the support plate 50. Concave portions 58a and 58b are formed in the inner side wall of the operation lever 56. A resilient member 60 engages with either of the concave portions 58a and 58b. The resilient member 60 includes a hollowed tubular case 62, a coiled spring 64 fixed in the case 62, and a ball 68 fixed to the free end of the spring 64. The ball 68 is always energized by the spring to resililently engage either of the concave portions 58a and 58b. The motor support plate 50 is located at a position (normal state) as indicated by a continuous line in FIG. 2, or at a position (operating state) as indicated by a dotted line, by normally operating the lever 56. In a normal state, the worm gear 44 mounted to the motor 48 fixed to the support plate 50, as illustrated by a continuous line, is in mesh with the spur gear 40 fixed to the drum 36. A rotating power from the motor 48 may accordingly be transmitted to the drum 36. When an operator pulls the lever 56, the support plate 50 is positioned in an operating state as indicated by a dash dot line. The gears 40 and 44 are released from their meshed state.

Returning to FIG. 1, a lever 66 for the bending operation is fixedly mounted at the bottom part to the rotating shaft 42 of the drum 36. The bending operation lever 66 is made of relatively solid resilient material. When an operator manually applies a force to the lever 66, it may bend to some extent, resisting its resilient force in the longitudinal direction of the endoscope 10. A knob 68 is fixed to the free end of the operation lever 66. The knob 68 protrudes outward from the operating section 16 of the endoscope system. A pressure-sensitive member such as a piezoelectric rubber 70 is attached to one of the two side walls of the curved operation lever 66, which are substantially normal to the rotation or a curved direction. The piezoelectric rubber 70 (also called a resistor wire distortion gauge) changes its resistance according to a compression stress or a tension stress applied to the rubber 70 by a manual bending of the operation lever 66. Thus, the piezoelectric rubber 70 serves as a detector for detecting the amount of operating force applied to the lever 66.

Figure 3:
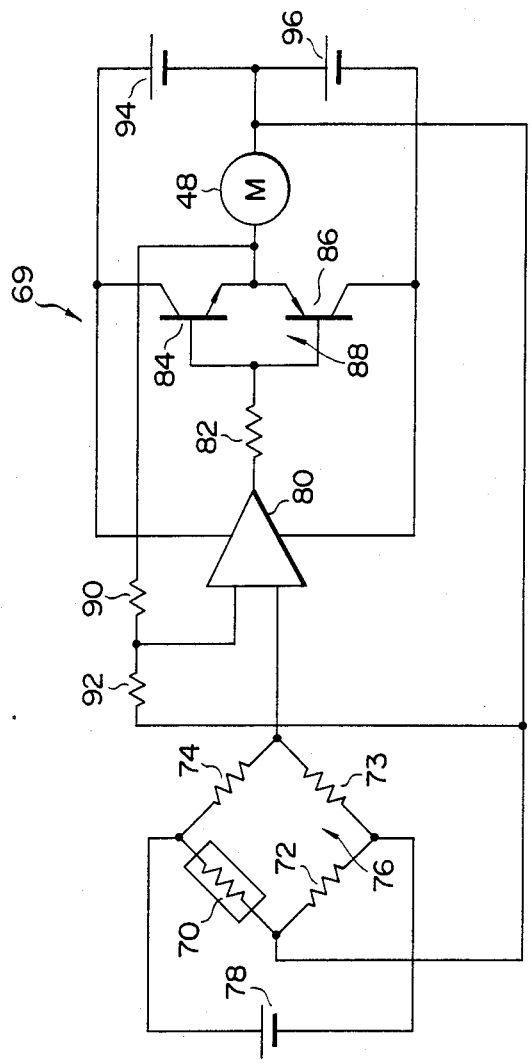
FIG. 3 is a circuit diagram of a control circuit for effecting a bending operation of an insertion section of the endoscope apparatus of FIG. 1.

FIG. 3 shows an electric circuit 69 for driving and controlling the motor 48 of a control section 71, preferably housed in the light source apparatus 12 of FIG. 1. The resistor line distortion gauge 70, together with resistors 72 to 74, make up a known bridge circuit 76. Two input terminals of the bridge circuit 76 are connected to a DC power source 78, as is well known. One of the input terminals of the bridge circuit 76 is connected to one of the input terminals of a differential amplifier 80 and the other input terminal of the bridge circuit 76 is connected to a first terminal of the motor 48. The output terminal of the amplifier 80 is connected in series through a resistor 82 to the base electrodes of an NPN type transistor 84 and a PNP type transistor 86 to form a buffer circuit 88. The emitter electrodes of the connected transistors 84 and 86 are connected to a second terminal of the motor 48. The emitter electrodes are also connected through a resistor 90 to the other input terminal of the amplifier 80 which is connected to the other output terminal of the bridge circuit 76 through a resistor 92. The first terminal of the motor 48 is connected to a negative terminal of a DC power source 94 and a positive terminal of a DC power source 96. A positive terminal of a DC power source 94 is connected to a collector electrode of the NPN transistor 84 and the amplifier 80. The negative terminal of the DC power source 96 is connected to the collector electrode of the PNP transistor 96 and the amplifier 80.

The operation of the endoscope system thus arranged, i.e., the first embodiment of the present invention, will now be described. When the bending operation lever 66 of the endoscope system 10 is not operated, no external force is applied to the lever 66. The resistance of the resistor wire distortion gauge 70 at this time balances the bridge circuit 76 in the operation. Accordingly, the bridge circuit 76 produces no output voltage.

When an operator operates the knob 68 coupled with the bending operation lever 66 for bending the fexible tube 19 of the insertion section, the lever 66 is bent. As a result of the knob operation, a compression stress or a tension stress is applied to the distortion gauge 70, thereby changing the resistance of the distortion gauge 70. A potential difference corresponding to that resistance change appears between the output terminals of the bridge circuit 76. The voltage corresponding to the potential difference is amplified by the amplifier 80 and is supplied to the buffer circuit 88 through the resistor 82. To be more specific, when the operator pulls the knob 68 to his side (toward the ocular section 18), the lever 66 is bent toward the ocular section 18 under the applied external force. Accordingly, the distortion gauge 70 is slightly stretched by the tension to increase the resistance of the gauge 70. At this time, a positive potential corresponding to the resistance change of the gauge is generated at the output terminal of the bridge circuit 76. Accordingly, a positive amplified signal is generated from the amplifier 80. The positive potential signal is applied to the base electrodes of the transistors 84 and 86 contained in the buffer circuit 88. At this time, the NPN transistor 84 is conductive while the PNP transistor 86 is nonconductive. With this circuit connection, the electric power from the DC power source 94 is supplied through the conductive transistor 84 to the motor 48. As a result, the motor 48 is rotated forward. The drive power from the forward rotating motor 48 is transmitted to the drum 36 through the gears 44 and 40, which are in mesh with each other. Then, the drum 36 rotates to wind up the angulation wire 38a and to bend the flexible tube 19 upward.

With the bending of the tube 19, the rotation of the drum 36 progresses and the lever 66, together with the rotating shaft 42 of the drum 36, turns progressively toward the ocular section 18. During the course of the turning of the lever 66, when the force applied to the knob 68 is stopped, the lever 66 is released from its bending state after a fixed time lag (from the stoppage of the application of the force to the knob). Finally, the tension exerted on the distortion gauge 70 becomes zero. At this time, the output voltage from the bridge circuit 76 is zero. The two transistors 84 and 86 forming the buffer circuit 88 are shut off and the motor 48 automatically stops.

During the period when the rotation of the drum 36 progresses with the bending operation of the tube 19, and the lever 66 and the rotating axis of the drum 36 as well turn toward the ocular section 18, if the operator continuously operates the knob 68, the lever 66 is further bent. Therefore, the bridge circuit 76 continuously produces a positive voltage. The positive voltage produced drives the motor 48 through the buffer circuit 88. The motor keeps rotating in the same direction. The flexible tube 19 is further bent. In this condition, if the operator pulls the knob 68 further, the output voltage of the bridge circuit 76 further increases. The signal level of the detection signal produced from the amplifier also further increases. The motor 48 rotates forward with a large torque to more forcibly bend the flexible tube 19.

Conversely, when the operator pushes the knob 68 away from the ocular section 18, the distortion gauge 70 attached to the lever 66 is compressed. With compression of the gauge 70, the resistance of the gauge 70 decreases to cause the bridge circuit 76 to produce a negative voltage at one of the output terminals of the bridge circuit 76. Therefore, the detection signal produced from the amplifier 88 has a negative potential level and the PNP type transistor 88 contained in the buffer circuit 86 is conductive. As a result, the DC power source 96 feeds a current to the motor 48 thereby rotating the motor 48. In this case, the direction of the rotation of the motor is opposite to that of the above-mentioned case, since the polarity of the current fed to the motor is opposite to that of the current in the above-mentioned case. With the reverse rotation of the motor 48, the drum 36 winds up the wire 38b to bend the flexible tube 19 downwardly.

As seen from the foregoing description, the first embodiment of the present invention may automatically bend the flexible tube 19 of the insertion section 14 strictly according to the operation of the knob 68. The pressure-sensing characteristic of the pressure-sensing element 70 used as a distortion gauge is highly sensitive. Further, the control circuit used has a response characteristic comparable to the pressure-sensing characteristic. Therefore, the endoscope system according to the present invention may easily effect a subtle bending of the insertion section according to the needs of the operator. Therefore, the insertion section eliminates the uncontrollable bending operation. Therefore, there is no danger of damaging the inner wall of the coeliac cavity of a living body. Thus, the endoscope system of the present invention is quite safe when it is applied for inspecting the coelom.

When the motor 48 and/or the control circuit of FIG. 3 malfunction during the course of use, it is very dangerous to pull out the insertion section 14 from the coeliac cavity while the flexible tube 19 is left bent. In such a situation, however, when the endoscope system of the present invention is used, the motor drive release lever 56 is operated to remove the worm gear 44 from the spur gear 40. That is, the bending operation mode of the endoscope may easily be changed from a motor drive mode to a manual operation mode. Therefore, the danger mentioned above may be avoided. The safety of the endoscope system of the present invention is thus further enhanced.

Figure 4:
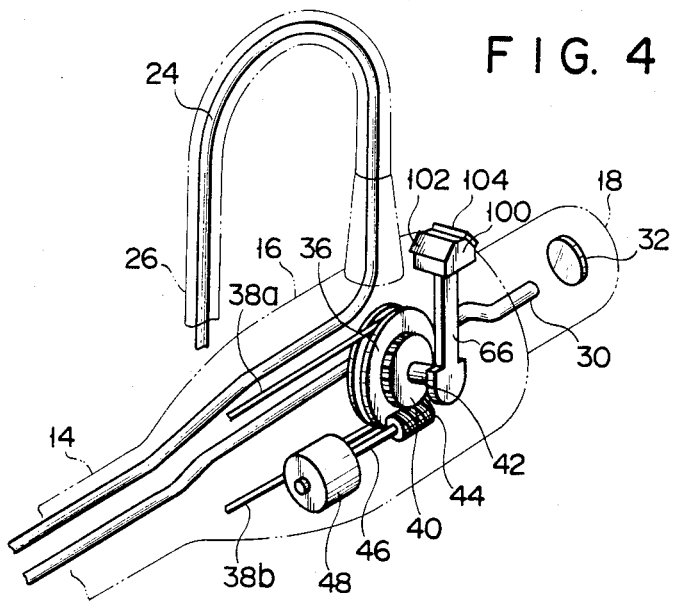
FIG. 4 is a perspective view of a major portion of an endoscope apparatus which is a second embodiment accordinG to the present invention.
Figure 5:
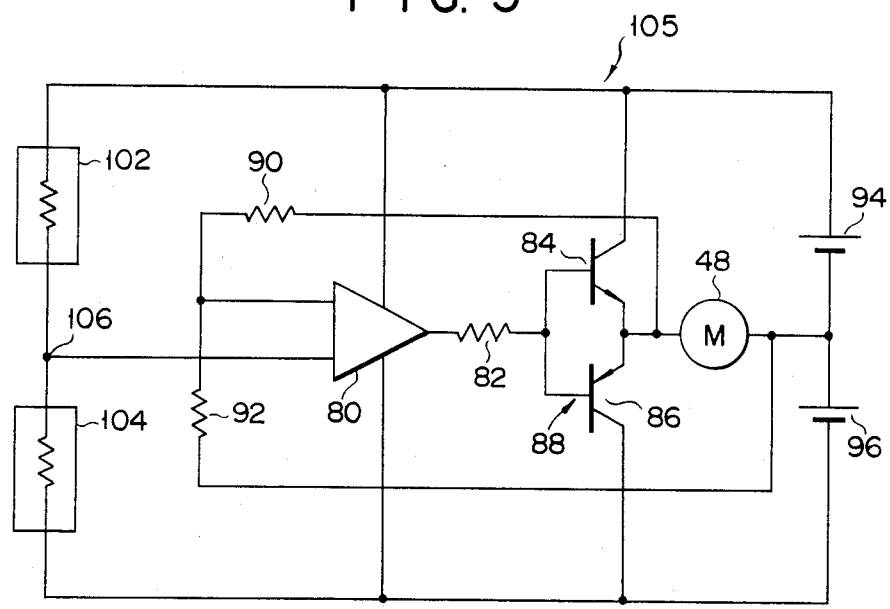
FIG. 5 is a circuit diagram of a bending operation control circuit used in the endoscope of FIG. 4.

Referring to FIGS. 4 and 5, there is shown a major part of a second embodiment of an endoscope according to the present invention. Like or equivalent portions in the figures of the drawings are designated by like symbols used in the drawings of the first embodiment, for simplicity.

In FIG. 4, a knob 100 mounted at the free end of the bending operation lever 66 is provided with two surfaces slanting toward the ocular section 18 and the insertion section 14 of the endoscope 10. Piezoelectric rubber pieces 102 and 104 as pressure sensors are attached to these slanted surfaces, respectively. FIG. 5 illustrates a control circuit 105 containing these piezoelectric pressure rubber pieces 102 and 104. These pieces 102 and 104 are each a kind of a pressure sensor which changes its resistance according to an external force applied thereto. These pieces are electrically connected to each other at a common junction 106. One end of the pressure sensor 102 is coupled with a positive terminal of a DC power source 94 at a given voltage. One end of the other pressure sensor 104 is connected to a negative terminal of the other DC power source 96 at the same voltage. The remaining circuit arrangement is similar to that of FIG. 3.

According to the second embodiment thus arranged, no external force is applied to the piezoelectric rubber pieces 102 and 104 so long as the knob 100 is not operated. Under this condition, in the control circuit shown in FIG. 5, the voltage drops across the pieces 102 and 104 are substantially equal to each other. The potential at the common junction 106 is substantially 0 V. No signal is produced from the amplifier 80. Two transistors 84 and 86 of the buffer circuit 88 are turned off so no electric power is supplied to the motor 86. The motor is at standstill.

For the bending operation of the flexible tube 19, the knob 100 is pulled by or turned toward the operator, i.e. the ocular section 18, for example. At this time, most of the force is applied to first piezoelectric rubber 102. The pressure sensor element 102 decreases its resistance according to the force applied. In the control circuit shown in FIG. 5, a positive voltage appears at the common junction 106 and is applied to one of the input terminals of the amplifier 80. The amplifier 80 produces an amplified detection signal of positive potential which is in turn applied to the buffer circuit 88. Upon receipt of the detection signal, the NPN type transistor 84 is conductive, while the PNP transistor 86 is turned off. A positive current flows from the DC power source 94 into the motor 48. The motor 48 rotates forward. The subsequent operation is almost the same as that of the first embodiment. The forward rotation of the motor 48 bends the insertion section 14 upward. If the application of the operating force applied to the knob 100 is discontinued, the potential at the common junction 106 in the control circuit shown in FIG. 5 is immediately returned to zero. Thus the motor 48 stops.

For bending the insertion section 14 downward, the knob 100 is pushed away from the ocular section 18. At this time, the resistance of the second pressure sensor 104 is decreased. The potential at the junction 106 of the control circuit of FIG. 5 is negative and the amplifier 80 produces an amplified detection signal with negative polarity. The negative detection signal turns off the NPN type transistor 84 and turns on the PNP type transistor 86. The DC power source 96 feeds a reverse current to the motor 48 through the conducting transistor 86. The motor 48 rotates in reverse. Subsequently, the drum 36 rotates in reverse as in the case of the reverse rotation of the motor in the first embodiment. The insertion section 14 is bent downward.

Also, the second embodiment as mentioned above may obtain effects similar to those obtained by the first embodiment. With the progressive bending of the insertion section 14, the lever 66 gradually turns with the rotating shaft 42 mounted to the rotating drum 36. A position of the knob 100 fixed to the lever 66 on the operating section 16 shifts linearly. An amount of the bending of the insertion section 14 may be quantitatively known on the basis of the degree of movement of the the knob 100.

Figure 6:
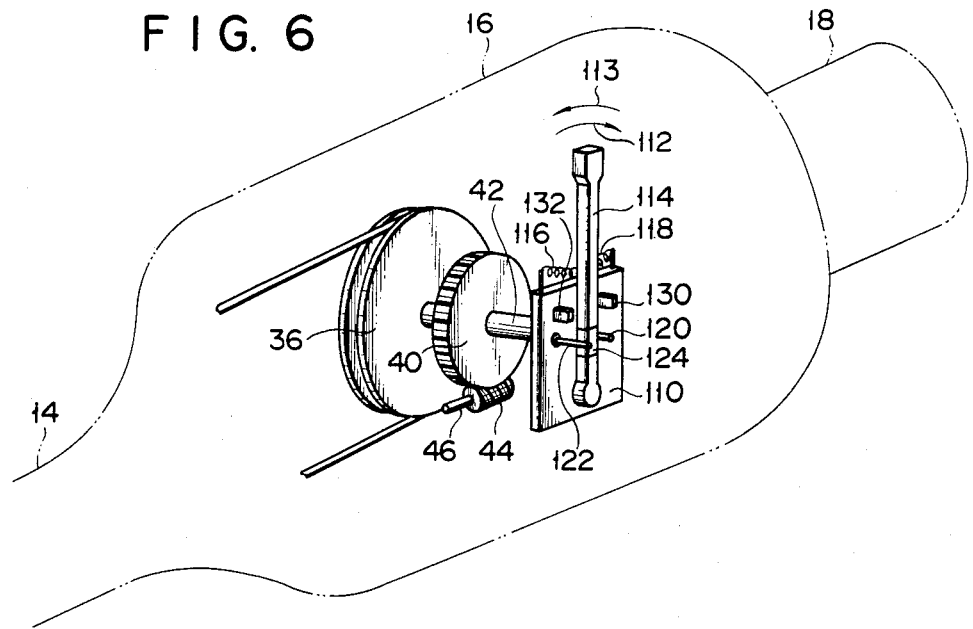
FIG. 6 shows a perspective view of a partial structure containing an operation lever portion and its periphery portion, which is provided for effecting a bending operation of the insertion section in an operating section of an endoscope system as a third embodiment of the present invention.
Figure 7:
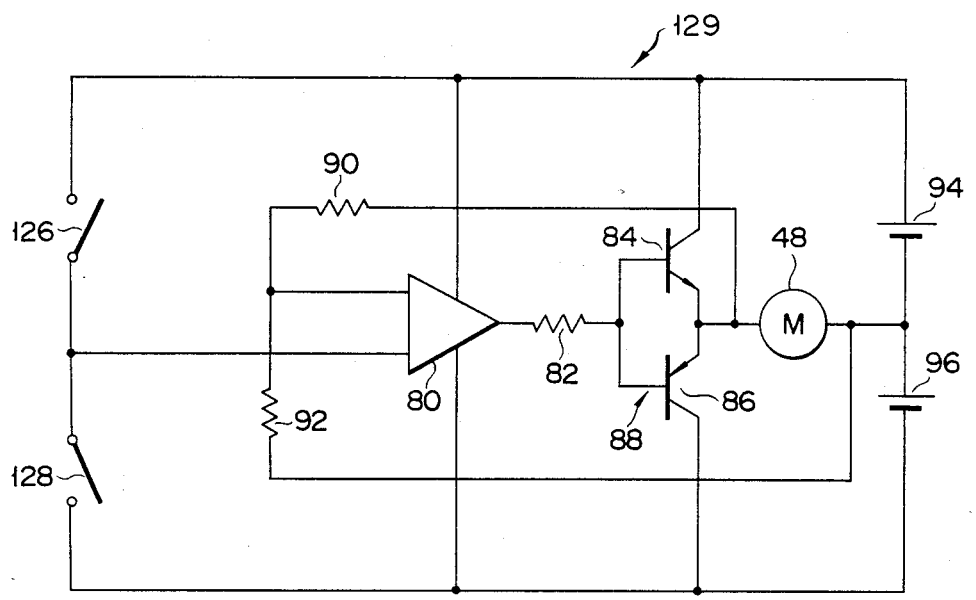
FIG. 7 is a circuit diagram of a bending operation control circuit containing the operation lever section of FIG. 6.

In FIGS. 6 and 7, there are schematically shown a bending operation lever and its related portion, and a control circuit for the lever, which are applied for a third embodiment of an endoscope system according to the present invention. The remaining arrangement is substantially the same as those of the above-mentioned embodiments.

In FIG. 6, a lever support plate 110 is fixed to the rotating shaft 42 of the drum 36. The plate 110 rotates integrally with the rotating shaft 42. The bending operation lever 114 is rotatably or swingably mounted at the base thereof on the plate 110. The lever 114 may turn in the direction of an arrow 112 or 113. The lever 114 is pulled in opposite directions by resilient members, for example, coiled springs 116 and 118. When no bending force is applied to the lever 114, it is set at a neutral position, as shown in FIG. 6. A pair of contact pins 120 and 122 made of resilient material are provided on the plate 110, while being located on both sides of the lever 114. The lever 114 at the neutral position equally divides a line connecting the contact pins 120 and 122. An electrode made of conductive material is attached to the portion of the lever 114 where the lever 114 is in contact with the contact pins 120 and 122. The pair of pins 120 and 122 and the lever electrode 124 equivalently made up a couple of switches 126 and 128 in the control circuit 129 of FIG. 7.

A pair of stopper members 130 and 132 are provided on the plate 110, wich a lever 114 interposed therebetween. The stopper members 130 and 132 are located by a predetermined small distance outside a turning range of the lever 114 which is defined by the contact pins 120 and 122. Accordingly, the lever 114 is in contact with the stopper members 130 or 132 after the lever electrode 124 contacts the contact pin 120 or 122 and the lever further travels outside of the turnable range. Thus, the stopper 130 or 132 prevents the lever from further turning.

In the third embodiment thus arranged, an operator turns the lever 114 in the direction of an arrow 112 in FIG. 6 until the lever 114 is in contact with the pin 120. The switch 126 is equivalently closed in the circuit shown in FIG. 7. At this time, as in the second embodiment, a positive current is fed from the DC power source 94 to the motor 48. The motor 48 rotates forward. The drum 36 also rotates forward to wind up the wire 38 and to bend the insertion section 14 upward. The plate 110 mounted to the rotating shaft 42 of the drum 36 is rotated clockwise during the bending operation of the insertion section 14, and rotates with the drum 36 in a unit manner. When the plate 110 rotates over a fixed angle, the contact pin 120 substantially departs from the lever electrode 124. At this time, the switch 126 in the FIG. 7 circuit is opened. The result is that the power supply to the motor 48 is automatically stopped and the motor 48 is stopped. When the lever 114 is turned at a fixed angle and held as it is, the motor stops at the time that the insertion section 14 is bent to a degree of the inclination angle of the lever 114. The insertion section 14 also stops its bending operation. If an operator progressively turns the lever 114, the insertion section 14 is progressively bent. The amount of actual bending of the insertion section may be known from an inclination angle of the lever 114. In the present embodiment, the switches in the control circuit of FIG. 7 are made up of the contact pins 120 and 122, and the lever electrode 124. These switches may of course be substituted by any other suitable switches using piezoelectric rubber, and the like.

Figure 8:
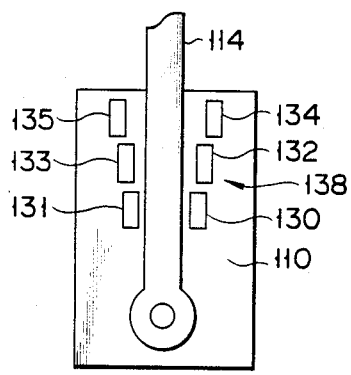
FIG. 8 is an explanatory diagram illustrating a modification of the operation lever section of FIG. 7.
Figure 9:
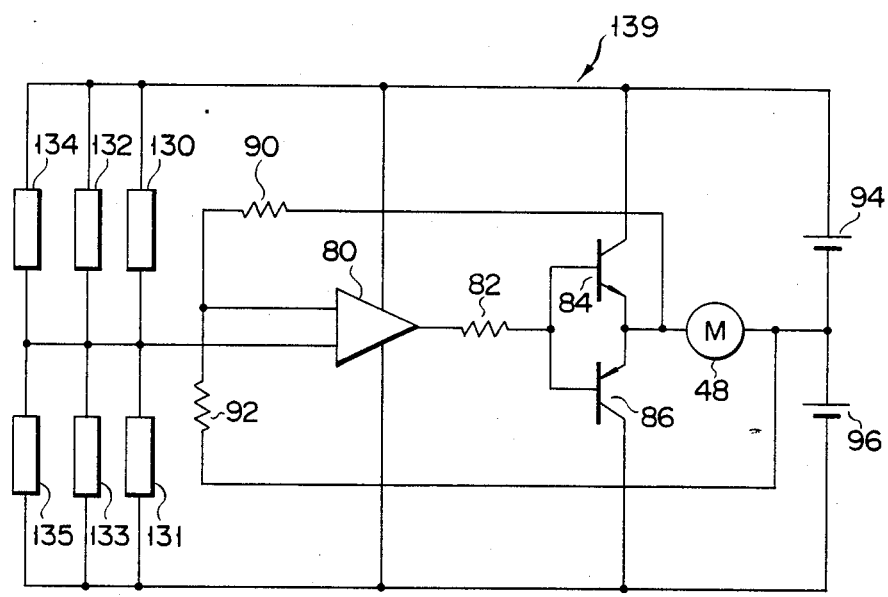
FIG. 9 is a circuit diagram of a bending operation control circuit including the operation lever section of FIG. 8.

FIGS. 8 and 9 schematically show a modification of the third embodiment of the present invention. Three pairs of piezoelectric rubber pieces 130 and 131, 132 and 133, and 134 and 135, which form a lever angle detecting switch section 138, are provided on the lever support plate 110, sandwiching the lever 114. A first pair of the piezoelectric rubber pieces 130 and 131 are located symmetrical with respect to the lever 114 at a neutral position. A second pair of the piezoelectric rubber pieces 132 and 133 are disposed wider than the first pair of the piezoelectric rubber pieces 130 and 131. A interval between a third pair of the piezoelectric rubber pieces 134 and 135 is wider than the interval between the second pair of the piezoelectric rubber pieces 132 and 133. When the lever 114 is turned in the direction of an arrow 112, for example, the lever 114 first contacts the piezoelectric rubber piece 130, and then the piezoelectric rubber pieces 132 and 134 in successive order.

In the control circuit 139 of FIG. 9, each pair of the piezoelectric rubber pieces are series-connected to each other, and three pairs of the piezoelectric rubber pieces are connected to one another in parallel. These pairs of the piezoelectric rubber pieces 130 to 135 are inserted between a positive terminal of the DC power source 94 and a negative terminal of the DC power source 96. The remaining arrangement is substantially the same as those of the other embodiments.

In the endoscope shown in FIGS. 8 and 9, it is assumed that an operator turns the bending operation lever 114 in the direction of an arrow 112. In this case, only the peizoelectric rubber piece 130 of the first pair of the piezoelectric rubber pieces 130 and 131 is pushed by the lever 114 to decrease its resistance. A positive voltage given by the descreased resistance is applied to the amplifier 80. The motor 48 forwardly rotates in a similar manner to that of the above-mentioned embodiments to bend the insertion section 14. Then, the lever 114 is further turned in the direction of an arrow 112. The piezoelectric rubber piece 132 of the second pair of the piezoelectric rubber pieces, together with the rubber piece 130 is also pushed by the lever 114 to decrease its resistance. A higher positive voltage given by the further decreased resistance is applied to the amplifier 80 to increase an output torque of the motor 48. Subsequently, when the lever 114 is still further forcibly turned, the rubber piece 134 is pushed together with the other two rubber pieces 130 and 132. At this time, a maximum positive voltage is applied to the amplifier 80 to maximize the output torque of the motor 48. Thus, as the turn of the lever 114 is greater, the output torque of the motor 48 is larger and the bending speed increases. Accordingly, the output torque of the motor 48 may subtly be adjusted by changing the operating force applied to the operating lever 114. And the bending speed of the output torque of the motor 48 may be changed in the same way. As a consequence, it is possible to realize a bending operation of the insertion section of the endoscope which is quick and accurate, and follows strictly the will of the operator.

Figure 10:
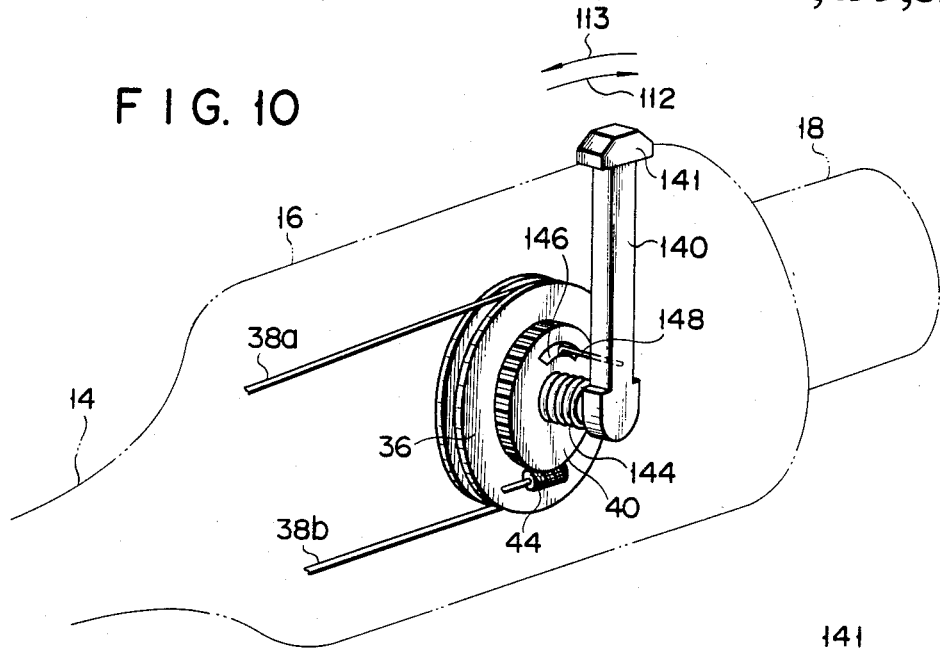
FIG. 10 is a perspective view of an operation lever section including a potentiometer provided in an operating section of an endoscope system which is a fourth embodiment of the present invention.
Figure 11:
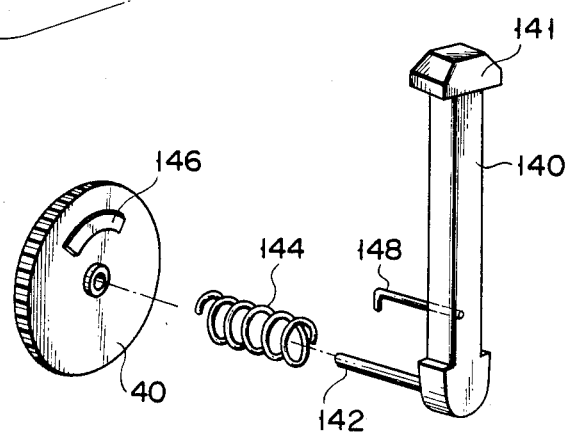
FIG. 11 is a perspective, exploded view illustrating in detail the structure of the operation lever section of FIG. 10.
Figure 12:
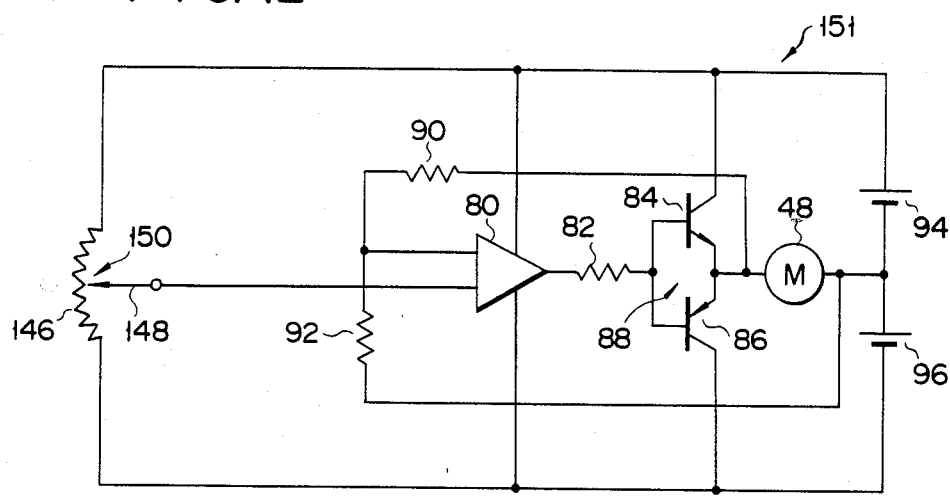
FIG. 12 is a circuit diagram illustrating a bending operation control circuit including the lever section of FIG. 10.

FIGS. 10 to 12 show a major part of an endoscope as a fourth embodiment of the present invention. In the present embodiment, a bending operation lever 140 made of solid material with a knob 141 at the free end thereof is coaxially and rotatably mounted through a shaft 142 to a spur gear 40 in mesh with a worm gear 40. The coiled spring 144 is wound around the periphery of the shaft 142 fixed to the lever 140. The spring 144 is fixed at one end to the spur gear 40 and at the other end to the lever 140. The lever 140 is turned from a neutral position shown in FIG. 5 to either direction of an arrow 112 or 113, resisting a strength of stability of the spring 144. A resistor member 146 like an arcuate strip is provided at a given location on the side wall of the spur gear 40 in opposition to the lever 140. A contact bar 148, disposed facing the resistor member 146, contacts at the L-shaped tip with the resistor member 146. The resistor member 146 and the contact member 148 make up a potentiometer 150 in the control circuit 151 of FIG. 12. The remaining arrangement of the present embodiment is substantially the same as those of the other embodiments.

In the endoscope incorporating such a potentiometer, the lever 140 is at a neutral position by means of the coiled spring 144. At the neutral position, the contact member 148 is contact with the resistor member 146 projecting from the lever 140 is electrically connected to the resistor member 146 at the center position of the resistor member 146, as shown in FIG. 12. Under this condition, an input voltage applied to the amplifier 80 is zero.

When the lever 140 is rotated resisting a strength of stability in one of the two opposite directions, the contact member 148, together with the lever 140, slides over the surface of the resistor member 146 toward one side. For example, the lever 140 is turned in the direction of an arrow 112, a positive voltage is applied to the amplifier 80. The motor 140 rotates forward and the insertion section 14 is bent upward. When the lever 140 is further turned in the same direction, the contact member 142 slides on the resistor member 146. A positive input voltage to the amplifier 80 raises. The output torque of the motor 48 increases to more greatly bent the insertion section upwardly. The present embodiment thus arranged may attain the useful effects comparable with those of the other embodiments.

Figure 13:
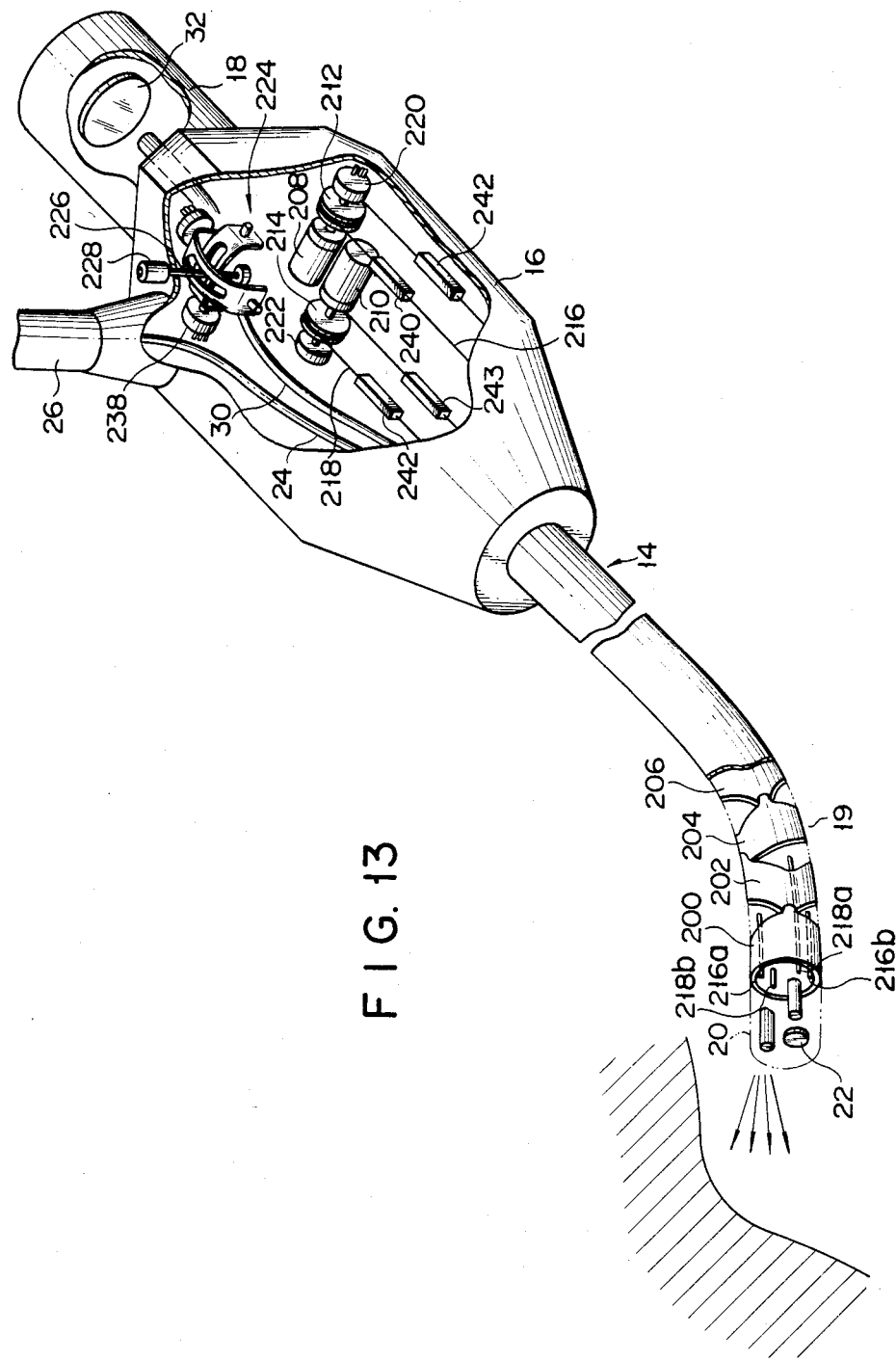
FIG. 13 is a partially broken perspective view of an overall endoscope apparatus which is a fifth embodiment of the present invention.
Figure 14:
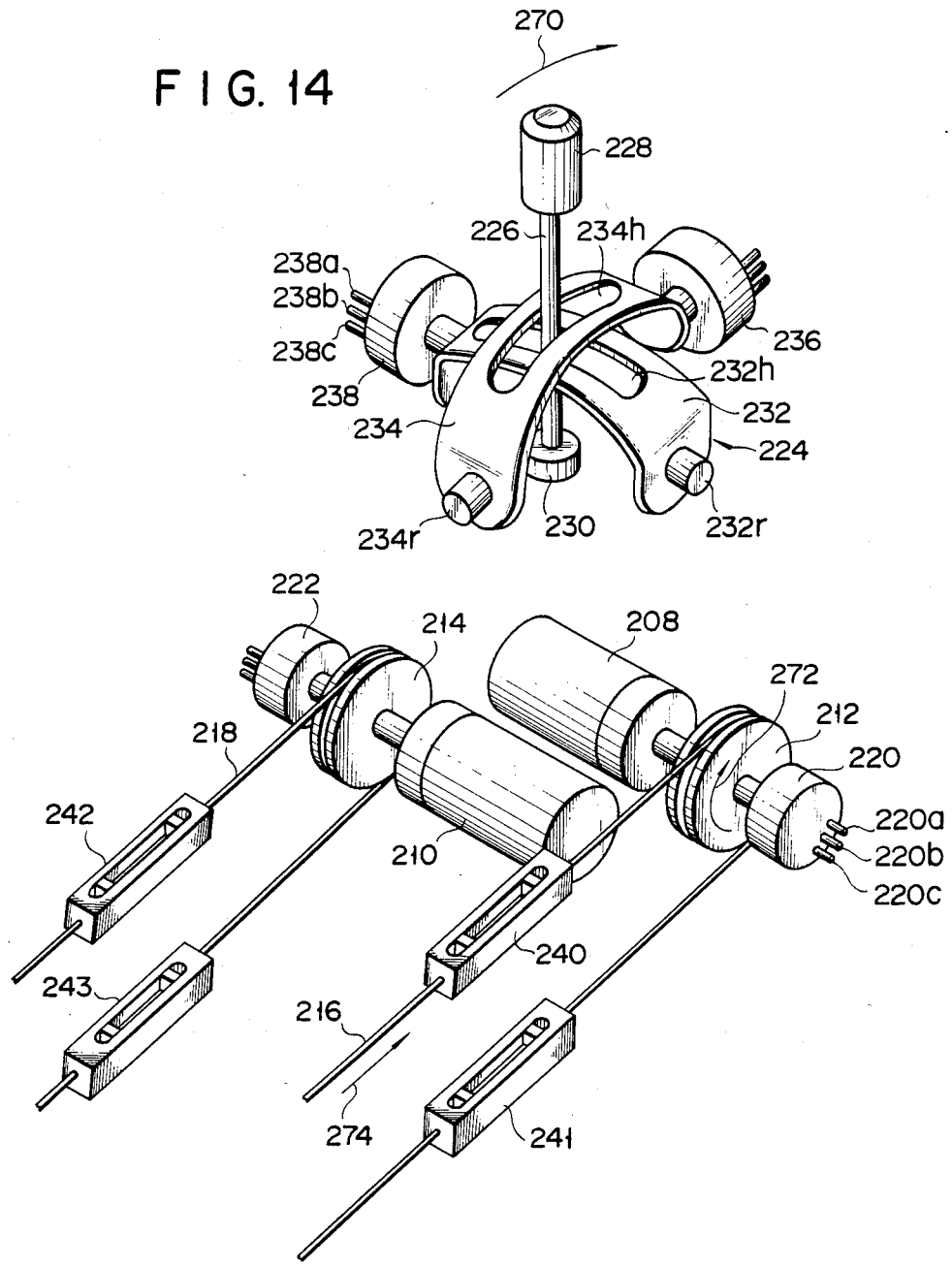
FIG. 14 shows enlarged perspective views of a bending operation lever provided in the operation section of the endoscope apparatus of FIG. 13 and a flexible tube drive section containing two motors.
Figure 15:
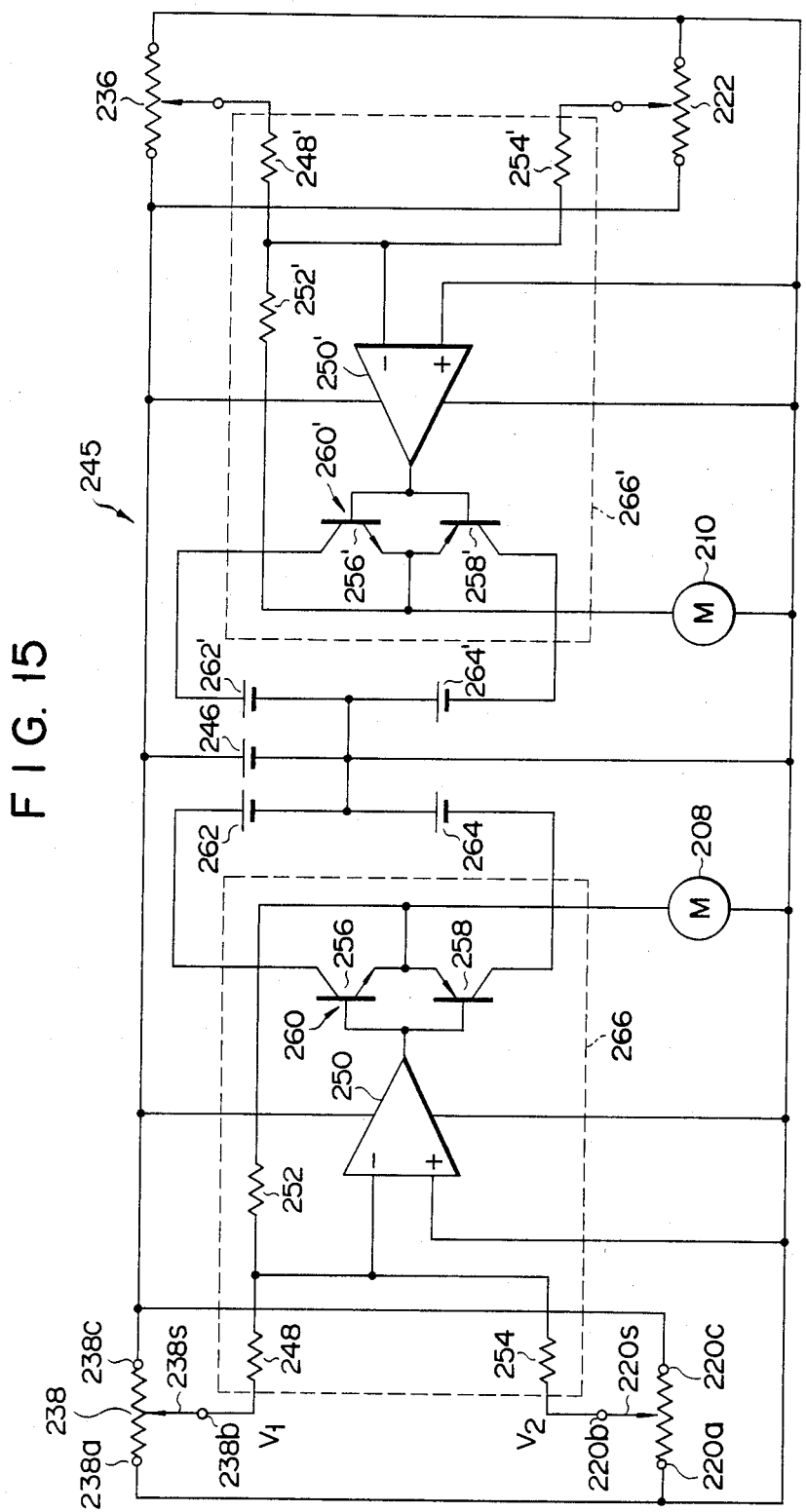
FIG. 15 is a circuit diagram of a bending operation control circuit containing a bending operation lever section and motors of FIG. 14, which is applied to the endoscope of FIG. 13.

FIGS. 13 to 15 show a fifth embodiment of an endoscope according to the present invention. Also in the present embodiment, like or equivalent portions are designated by like reference symbols, for simplicity.

As well illustrated in FIG. 13, the flexible tube 19 of the insertion section 14 includes a plurality of joint members 200, 202, 204, 206, . . . These joint members are arranged in a known manner so that the flexible tube 19 can turn the end portion 20 in a desired direction by bending the flexible tube 19 at a desired bending amount and in a desired direction. A couple of motors 208 and 210 are housed in the operating section 14 of the endoscope. Each of the motors 208 and 210 is rotatable in forward and reverse directions. Drum members 212 and 214 are mounted to the rotating shafts of the motors 208 and 210, respectively. The drums 212 and 214 rotates forwardly or reversely according to the rotating direction of the motors 208 and 210, respectively. Angulation wires 216 and 218 are wound around the grooves formed on the peripheries of the drum members 212 and 214, respectively. The wire 216 moving with the rotation of the motor (first motor) 208 is passed through the flexible tube 19 of the insertion section 14. A pair of wire terminals 216a and 216b of the wire 216 are fixed to the joint member 200 located at the distal end of the flexible tube 19. These wire terminals 216a and 216b are disposed oppositely or angular-distanced at about 180°. The wire 218 moving with the rotation of the other motor (second motor) 210 is also passed through the flexible tube 19. A pair of wire terminals 218a and 218b of the wire 218 are fixed to the joint member 200, while being angular distanced at about 180°. The pair of the wire terminals 218a and 218b is shifted by about 90° from the pair of the wire terminals 216a and 216b. Potentiometers 220 and 222 are mounted to the drums 212 and 214, respectively. As illustrated in FIG. 14 in an enlarged manner, the potentiometer 220 is provided with terminals 220a, 220b and 220c, and a sliding terminal 220s (FIG. 15). The sliding terminal forwardly or reversely interlocking with the first motor 208. An output voltage from the potentiometer 220 changes with a rotation of the drum 212 interlocked with the first motor 208. The potentiometer 222 is also constructed like the potentiometer 220.

The operating section 16 is provided with a bending operation member 224 for controlling a bending operation of the insertion section 14. As well illustrated in FIG. 14, the bending operation member 224 includes a lever 226 freely turned about its bottom end as a supporting point in any desired direction, and a knob 228 mounted at the free end of the lever 226, which exists outside the operating section 16, so as to allow a manual operation by an operator. The bending operation member 226 may be turned in any direction including back and forth, and right and left directions, from the neutral position (where the operation member 226 is upright at a base 230 like a disc). The first and second motors 208 and 210 are driven corresponding to a direction and an amount of the turn of the operating member, i.e. an operation amount of the operating member.

In FIG. 14, the bending operation lever 226 is mounted at the bottom end to the base 230. The lever 226 passes through elongated holes 232a and 234a formed in arcuate frames 232 and 234, which are disposed on the cross and one frame upon another. Further, these frames 232 and 234 are arcuately turned about the shafts 232r and 234r when the operation lever 226 is operated. The potentiometers 236 and 238 are mounted to the frame shafts 232r and 234r, respectively. The sliding terminals of these potentiometers 236 and 238 rotate with the rotation of the frames 232 and 234 to generate the output voltages respectively corresponding to the rotating amounts of the frames. Buffers designated by reference numerals 240, 241, 242 and 243 absorb deflection of the wires 216 and 218, when it is produced therein, for preventing these wires from contacting other neighboring parts of the operating section 16.

Turning now to FIG. 15, there is shown an electric circuit 245 for controlling a bending operation of the insertion section of the endoscope according to the present embodiment. The potentiometer 238 is connected across a DC power source 246 through terminals 238a and 238c thereof. The terminal 238b of the potentiometer 238 is connected through a resistor 248 to a first input terminal of an operational amplifier 250 and through a feedback resistor 252 to the first motor 208. The other potentiometer 220 is connected to the potentiometer 238 in parallel. The terminal 220b is connected through a resistor 254 to a second input terminal of the operational amplifier 250. The output terminal of the operational amplifier 250 is connected to the base electrodes of two transistors 256 and 258 back-to-back connected to form a current amplifier 260. The emitters of the NPN transistor 256 and the PNP transistor 258 are interconnected and connected to the first motor 208. Two DC power sources 262 and 264 are connected between the collectors of these transistors 256 and 258. The operational amplifier 250, and the current amplifier 260 including the transistors 256 and 258 make up a servo control circuit 266.

A bending operation control circuit including the second motor 210 and the frame 234 has substantially the same arrangement as that of the bending operation control circuit including the first motor 208 and the frame 232. No further explanation of the circuit arrangement including the motor 208 will be given for avoiding duplicate explanation. In the control circuit including the motor 210, like circuit components are designated by like but primed numerals in the control circuit including the motor 208, for simplicity of illustration.

The operation of the above-mentioned embodiment will now be described. To start, the operation lever 226 is turned in the direction of an arrow 270 in FIG. 14, for example. The rotating frame 232 is pushed by the lever 226 to rotate in the arrow direction 270. At this time, the sliding terminal 238s of the potentiometer 238 slides towards the terminal 238c according to the rotating amount of the rotating frame 232. The terminal voltage $V_1$ at the terminal 238b show in FIG. 15 increases and exceeds the terminal voltage $V_2$ at the terminal 220b. As a result, a negative voltage is produced at the output terminal of the operational amplifier 250. The PNP type transistor 258 is rendered conductive. The voltage proportional to the output voltage is applied to the first motor 208. Thus the motor 208 rotates. Then, the drum 212 rotates in the arrow direction 272 in FIG. 14 to pull the wire 216 in the arrow direction 274, for example. One of terminal end 216b, for example, of the wire 216 is pulled to bend the flexible tube 19 of the insertion section 14 downwardly (FIG. 13). Under this condition, the sliding terminal 220s of the potentiometer 220 mounted to the drum 212 associated with the first motor 208 also slides to the terminal 220c. The terminal voltage $V_2$ (FIG. 15) at the terminal 220b also increases.

When the terminal voltage $V_2$ at the terminal 220b is substantially equal to the terminal voltage $V_1$, the output voltage from the operational amplifier 250 is substantially 0 V. The PNP transistor 258 is turned off and the first motor 4 stops its rotation. Thus, the output voltage $V_1$ of the potentiometer 238 provided on the bending operation member 224 changes according to the operation amount of the operation lever 226. During the changing of the voltage $V_1$, the first motor 208 rotates with the operation of the first motor 208. At this time, the potentiometer 220 operates with the rotation of the motor 208 to produce the output voltage $V_2$ according to the rotating amount of the motor 208. When the difference between the output voltages $V_1$ and $V_2$ is zero, the motor 208 immediately stops.

In the fifth embodiment, the operating amount of the bending operation lever 226 is electrically detected by the potentiometers 236 and 238. The operation amounts of the drums 212 and 214 directly coupled with the motors 208 and 210 are electrically detected by the potentiometers 220 and 222, respectively. This feature remarkably simplifies the construction of the endoscope system and also reduces the manufacturing cost. Further in the fifth embodiment, the output voltages from the potentiometers 236 and 238 associated with the operation lever 226 and the potentiometers 220 and 222 associated with the first and second motors 208 and 210 are electrically processed in the servo control circuits 266 and 266′, respectively. Through this processing, the operation amounts of the first and second motors 208 and 210 are made to accurately follow the operation amount of the bending operation member 244. Because of this feature, the insertion section 14 of the endoscope system may quickly and accurately be bent in any direction including back and forth, and right and left directions, strictly according to the will of the operator.

Figure 16:
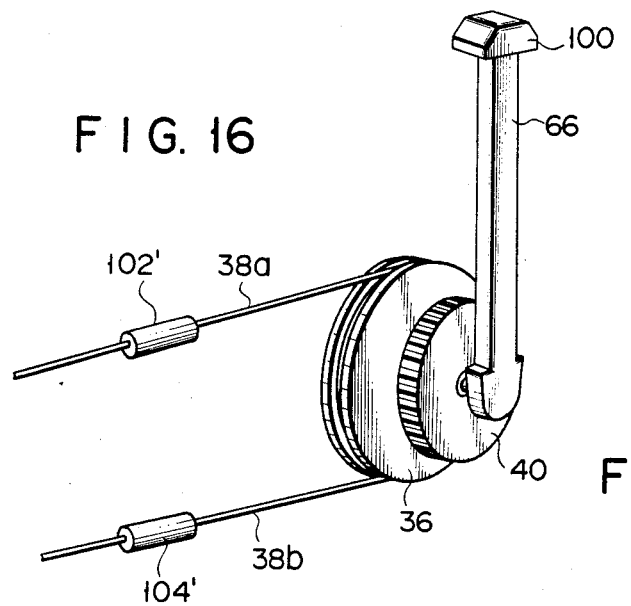
FIG. 16 shows a perspective view of a modification of a bending operation lever of the embodiment shown in FIGS. 4 and 5.

Although the present invention has been shown and described with respect to particular embodiments, nevertheless, various changes and modifications which are obvious to a person skilled in the art to which the spirit, scope and contemplation of the invention. For example, in the second embodiment of the endoscope shown in FIGS. 4 and 5, the pressure sensing elements 102 and 104 for detecting the operating force applied to the lever 66 are mounted to the knob 100 attached to the lever 66. The pressure sensing elements may be attached to proper locations of the angulation wires 38a and 38b wound around the drum 36, as shown in FIG. 16. In this case, the pressure sensing elements are used for detecting the force applied to the wires.

Figure 18:
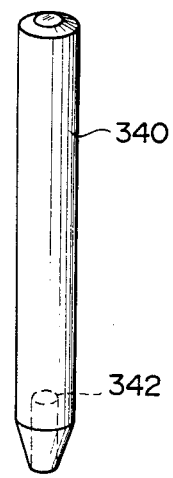
FIG. 18 is a perspective view of an auxiliary lever applied to the operation lever knob of FIG. 17 for improving operability in a manual operation of the operation lever.
Figure 17:
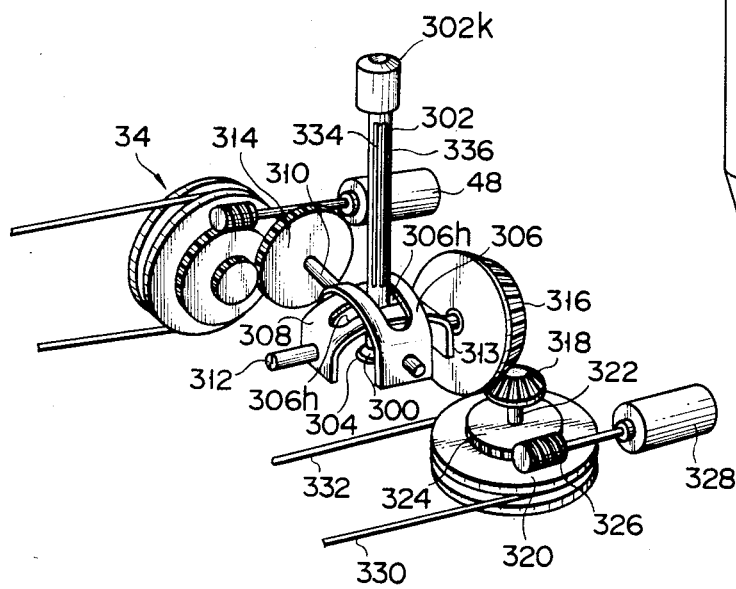
FIG. 17 is a perspective view of the bending operation lever section of the embodiment shown in FIGS. 1 to 3, which may be turned in every direction.

In the embodiment shown in FIGS. 1 to 3, the flexible tube 19 of the insertion section 14 is bent upward or downward. It is evident that the bending direction of the flexible tube may be up and down, and right and left. A major part of an embodiment of an endoscope in which the flexible tube 19 are bendable in various directions, as just mentioned, is illustrated in FIGS. 17 and 18. In the present embodiment, a ball member 300 is provided at the bottom end of the operation lever 302. The ball member 300 is fitted in a spherical bearing 304 so as to allow the bending operation lever 302 to be turned in every direction. a couple of rotating members 306 and 308 which are rotatable in the directions orthogonal to each other, are provided around the base portion of the lever 302. The rotating members 306 and 308 are rotatably supported by shafts 310 and 308, which are arranged along the rotating members, respectively. The rotating members 306 and 308 have elongated holes 306h and 308h extending along the shafts, respectively. The bending operation lever 302 is passed through these holes. The shaft 310 of the rotating member 306 rotating in the back and forth direction is coupled with the rotating shaft 42 in the bending mechanism 34, through an intermediate gear 314, as in the first embodiment (FIG. 1). The shaft 312 of the rotating member 313 rotatable in the right and left directions is coupled with the rotating shaft 322 of the drum 320 for bending the flexible tube in the right and left directions, through the intermediate gears 316 and 318. The gear 324 is mounted to the gear 322 which is further in mesh with a warm gear 326 driven by the motor 328. Wires 330 and 332 for bending the flexible tube in the right and left directions are wound around the drum 320. Resistor wire gauges 334 and 336 like those of the first embodiment are respectively attached to the side wall of the operation lever 302 facing the back and forth directions and the side wall of the lever facing the right and left directions. The flexible tube 19 of the insertion section 14 (FIG. 1) is bent by driving the motors 48 and 328 by the signals derived from the resistor wire gauges 334 and 336.

The releasing mechanism as shown in FIG. 2 in also assembled into the present embodiment. Accordingly, when the motors 48 and 328 are trouble, the bending operation may easily be done by means of the bending operation lever 302. For more easy operation of the lever 302, it is preferable to use an auxiliary lever 340 provided with a hole into which the knob 302k of the operation lever 302 is fitted when the auxiliary lever is used, as shown in FIG. 18.

Additionally, in the fifth embodiment, the bending operating section is not necessary provided in the frame body of the endoscope. It may be provided in the light source unit. Alternatively, it may be constructed in a separate unit for remotely controlling the bending operation of the insertion section 14.

What is claimed is:
1. An endoscope apparatus comprising:
 (a) an insertion section bendable in a body cavity upon insertion thereinto;
 (b) an endoscope body mechanically coupled to said insertion section;
 (c) motor means in said endoscope body for generating rotating torque for bending said insertion section;
 (d) an operation lever member provided in and protruding at least partially from said endoscope body so as to be manually operable by an operator;
 (e) bending mechanism means in said insertion section and said endoscope body and coupled to said motor means, to said insertion section and to said operation lever member, for bending said insertion section and rotating said operation lever member by the torque from said motor means;
 (f) lever operating amount detecting means mounted to said operation lever member, for changing the resistance value thereof in response to elastic deformation in said lever member when an operator operates said lever member and external pressure is applied and, for detecting an operating amount of said lever member; and
 (g) control circuit means, electrically connected to said motor means and said lever operating amount detecting means, for supplying electricity to said motor means in response to changes in the resistance of said operation lever member, thereby causing said bending mechanism means to bend said insertion section and to rotate the lever member in substantially the same direction as the direction of lever operation to decrease the elastic deformation of said operation lever member and, for shutting off said motor means when the change in resistance of said lever operating amount detecting means reaches substantially zero in response to the elastic deformation of said lever member reaching substantially zero, to thereby control the bending of said insertion section such that the bending is automatically stopped when the insertion section is bent by an amount corresponding to said lever operation amount; said control circuit means including switching transistor means electrically connected to said lever operating amount detecting means, for controlling the power supply to said motor means, in response to a change in the resistance value of said lever operating amount detecting means, in such a manner that said motor means is rotated forward or backward in response to the change in the resistance value of said lever operating amount detecting means.

2. An endoscope apparatus according to claim 1, wherein said bending mechanism means comprises:
  wire means passed through said body and said insertion section, and fixed to an end portion of said insertion section; and
  drum means, mechanically coupled with said wire means, said lever member and said motor means, for rotating in response to the rotation of said motor means, to thereby drive said wire means so as to bend said insertion section, said drum means simultaneously rotating said lever member.

3. An endoscope apparatus according to claim 2, said lever member being of resilient material so as to be deflectable in a direction substantially normal to the direction of extension of said lever member and of an applied external force and is able to return to its original state, said lever member having a base end mechanically coupled with said drum means so as to rotate within an arcuate range with the rotation of said drum means; and said lever operating amount detecting means being mounted to said deflectable lever member and having a resistance value changing in response to a compression stress and tension stress selectively generated in said lever member when said lever member is deflected as the result of the application of the external force.

4. An endoscope apparatus according to claim 3, wherein said bending mechanism means further includes:
  worm gear means mechanically coupled between said motor means and said drum means, for rotating in accordance with the rotation of said motor means to transmit the rotational torque of said motor means to said drum means.

5. An endoscope apparatus according to claim 4, comprising releasing means provided in said endoscope body for releasing the meshing state of said worm gear means with said drum means at a desired time to allow said drum means to be manually operable.

6. An endoscope apparatus according to claim 2, wherein said control circuit means includes:
  plate means mechanically coupled with said drum means and swingable with said drum means, for rotatably supporting the base end of said lever means so that said lever means is swingable in an angular range smaller than 180° according to the operating force applied;
  means provided on said plate means for resiliently holding said lever means at a predetermined neutral position during the normal state, said lever means being made of solid material; and
  switch means provided on said plate means, for starting the switching operation to feed electric power to said motor means when said lever means responds to the operating force applied to turn about the base end at a predetermined angle, and for stopping the switching operation when said plate means rotates at a predetermined angle with said drum means, and the operation force applied to said lever means is equivalently maintained and said lever means keeps said turned state, so as to prevent the power supply to said motor means.

7. An endoscope apparatus according to claim 6, wherein said switch means changes its resistance value according to an angle of said turned lever means so as to feed a current changing with the angle of said lever means.

8. An endoscope apparatus according to claim 2, wherein said control circuit means includes:
  a sliding member fixed to said lever means, said sliding member protruding from said lever means made of solid material toward said drum means;
  a resistor provided at a location of said drum means corresponding to a trace of the movement of a tip portion of said sliding member so as to electrically contact said sliding member, said resistor having terminals applied with a predetermined DC voltage; and
  motor current control circuit means electrically connected to said motor means and said sliding member, for detecting a potential change at said sliding member generated when said sliding member rotates to continuously slide on said resistor while said sliding member keeps the electrical contact with said resistor, with the turn of said lever means caused by the operation force applied, and for supplying said motor means with a current changing in response to the potential change detected.

9. An endoscope apparatus according to claim 8, further comprising spring means located between said lever means and said drum means, for applying a resilient force to said lever means so as to keep a neutral position where said sliding member electrically contacts said resistor at substantially center point of said resistor.

10. An endoscope apparatus according to claim 9, wherein said motor current control means shuts off the power supplied to said motor means when said sliding member electrically contacts said resistor at a substantial center point of said resistor where the potential at said sliding member is substantially zero when the application of the operating force ceases and said lever means returns to the neutral position by said spring means, or when said resistor rotates with the rotation of said drum means caused by said motor means, while keeping its electrical contact with said sliding member.

11. An endoscope apparatus according to claim 2, wherein said control circuit means includes:
  a first potentiometer with a first sliding member rotating with the turning operation of said lever means and two power source terminals across which a predetermined voltage is applied;
  a second potentiometer with a second sliding member mechanically coupled with said drum means so as to rotate with the rotation of said drum means interlocking with said motor, and two power source terminals across which the DC voltage is applied;

comparator means electrically connected to said first and second sliding members of said first and second potentiometers, for detecting a relative amplitude between first and second potentials at said sliding means to produce a signal representing the detected relative magnitude; and motor current control means electrically connected to said comparator means and said motor means, for controlling the power supply to said motor means in response to said detection signal.

* * * * *